(12) United States Patent
McIntosh et al.

(10) Patent No.: US 6,485,932 B1
(45) Date of Patent: Nov. 26, 2002

(54) COMPOSITION COMPRISING IMMUNOGLOBULIN

(75) Inventors: Ronald Vance McIntosh, North Berwick (GB); Anne Gillian Welch, Fife (GB)

(73) Assignee: Common Services Agency (GB)

( * ) Notice: Subject to any disclaimer, the term of this patent is extended or adjusted under 35 U.S.C. 154(b) by 0 days.

(21) Appl. No.: 09/381,600

(22) PCT Filed: Mar. 18, 1998

(86) PCT No.: PCT/GB98/00812

§ 371 (c)(1),
(2), (4) Date: Oct. 25, 1999

(87) PCT Pub. No.: WO98/42376

PCT Pub. Date: Oct. 1, 1998

(30) Foreign Application Priority Data

Mar. 20, 1997 (GB) .............................................. 9705810

(51) Int. Cl.⁷ ......................... C12P 21/06; A61K 38/46; A61K 39/395; A61K 39/40; A61K 39/42
(52) U.S. Cl. ................ 435/68.1; 424/130.1; 424/94.66; 424/142.1; 424/177.1; 424/178.1; 424/179.1; 424/183.1
(58) Field of Search ...................... 435/68.1; 424/177.1, 424/130, 142.1, 94.66, 130.1, 178.1, 179.1, 183.1; 530/387.1

(56) References Cited

U.S. PATENT DOCUMENTS

| 4,499,073 A | | 2/1985 | Tenold |
| 5,871,736 A | * | 2/1999 | Bruegger et al. |

FOREIGN PATENT DOCUMENTS

| EP | 0702960 A1 | | 2/1995 |
| WO | WO 96/07429 | * | 3/1996 |
| WO | WO96/35710 | | 11/1996 |

OTHER PUBLICATIONS

Japanese Abstract, Publication No. 56015215, Feb. 14, 1981, *Preparation of Human Immunoglobulin for Intravenous Injection with Immobilized Pepsin Gel* (1981).

* cited by examiner

Primary Examiner—Christopher R. Tate
Assistant Examiner—Michele Flood
(74) Attorney, Agent, or Firm—Myers Bigel Sibley & Sajovec, P.A.

(57) ABSTRACT

Liquid compositions for intravenous administration that comprise an aqueous solution of immunoglobulin and methods of preparing such compositions are disclosed. The solution has a pH in the range of 5.0 to 5.8 and an ionic strength is the range 0.02 to 0.25. The liquid compositions are formulated so as to be stable upon storage such that the immunoglobulin does not substantially aggregate nor degrade and maintains acceptable levels of anti-complementary activity, PKA activity and kallikrein activity during storage for an extended period at a temperature in the range of 4° C. to 25° C.

29 Claims, 1 Drawing Sheet

FIGURE 1

PREPARATION OF IMMUNOGLOBULIN FROM HUMAN BLOOD PLASMA

BY COLD ETHANOL FRACTIONATION

COMPOSITION COMPRISING IMMUNOGLOBULIN

The present invention relates to a liquid composition for intravenous administration which comprises an aqueous solution of immunoglobulin. The immunoglobulin is generally immunoglobulin G (IgG) derived from human blood plasma.

Immunoglobulin for intravenous infusion has been in clinical use for several years. The product is available as a lyophilised dry formulation or in some cases, as an intravenously injectable liquid formulation. The dry formulation, presented as a vial containing for example 5 g of immunoglobulin, requires to be reconstituted into an injectable solution before use and doses of up to 1 g per Kg body weight per day are recommended for several clinical indications. Such large doses require a number of vials to be reconstituted into an injectable formulation, which is inconvenient and time consuming. There are therefore considerable advantages in providing a ready to use injectable formulation. However, such liquid formulations require to be stable on long term storage.

Conventionally, IgG is isolated from blood plasma using ethanol fractionation processes. These include the original Cohn-Oncley methods which are still in use principally in the USA and various other established modifications of that method which are used mainly in Europe (for a review of ethanol fractionation processes see Ethanol Precipitation by Kistler P. and Friedli H. in Methods of Plasma Protein Fractionation, J. M. Curling, ed., Academic Press, Inc., New York, 1980). A disadvantage of ethanol, namely its potential for denaturing proteins, is offset by using low processing temperatures and hence these methods are generally referred to as "cold ethanol fractionation". Cold ethanol fractionation processes all depend on the manipulation of five variables, ie. ethanol concentration, pH, ionic strength, temperature and protein concentration to achieve the selective separation of proteins into different precipitates which, by convention, are known as Fractions. Fraction II is the principal immunoglobulin bearing precipitate in the cold ethanol fractionation of human blood plasma.

For some time preparations for the intramuscular administration of immunoglobulin have been formulated from Fraction II. However, the intravenous infusion of these preparations has been found to cause severe adverse reactions, resembling anaphylaxis (ie. cardiovascular collapse and bronchospasm), in recipients (see Immunoglobulins: Characteristics and uses of intravenous preparations, Alving B. M. and Finlayson J. S., eds, US Dept. of Health and Human Sciences Publication No. (FDA)-80-9005, 1979). These severe adverse reactions are now known to be caused principally by the presence of aggregates of IgG molecules and the contamination of Fraction II with trace quantities of vasoactive blood plasma enzymes such as pre-kallikrein activator (PKA) and kallikrein. Aggregated immunoglobulin can bind and activate the complement group of blood plasma proteins (so called "anti-complementary activity") and the activation of the complement system results in the generation of the complement peptides C5a and C3a which are anaphylatoxins. It is also known that the administration of PKA and kallikrein in physiological significant quantities can cause severe hypertension and cardiovascular collapse.

Thus in the preparation of a formulation of immunoglobulin for intravenous infusion attention needs to be paid to the above issues. A number of approaches have been taken to solving this problem. These include, altering the processing of Fraction II in order to prevent aggregate formation; further purification of the immunoglobulin from Fraction II so as to remove aggregates and other contaminating plasma proteins and the treatment of immunoglobulin from Fraction II with very low levels of a proteolytic enzyme such as pepsin to dissociate any aggregates and residual PKA and kallikrein. (For a review of the production of Immunoglobulin for intravenous infusion see Methods for the Production of IVIG Preparations and Analysis of IVIG Preparations Available, by Lundblad J. L. and Schroeder D. D. in Clinical applications of intravenous immunoglobulin therapy, P. L. Yap, ed., Churchill Livingstone Inc., New York, 1992). The use of pepsin in this way has been found to be optimum at a relatively low pH, eg. 4.0. Additionally it is well understood in the art that such a low pH treatment is an effective virus inactivation procedure (see Reid, K. G. et al. Vox Sang. 55 p75–80, 1988. Potential contribution of mild pepsin treatment at pH4 to the viral safety of human immunoglobulin products).

In fact, preparations of human immunoglobulin for intravenous infusion are required to meet certain standards, such as those recommended by the European Pharmacopoeia Commission which sets out guidelines for inter alia distribution of molecular size, anti-complementary activity, PKA and that the method of preparation includes a step or steps that have been shown to inactivate known agents or infection (see European Pharmacopoeia Third Edition published June 1996 to replace the second edition on Jan. 1, 1997, Monograph number 1997: 0918, Human Normal Immunoglobulin for Intravenous Administration).

The majority of human immunoglobulin products for intravenous infusion on the market currently are in the form of freeze dried preparations to provide stability on shipment and storage. These preparations must be reconstituted before use which can be inconvenient and time consuming as described earlier. In addition, liquid compositions of immunoglobulin for intravenous infusion are also available.

U.S. Pat. No. 4,499,073 (Cutter Laboratories Inc.) describes the production of an intravenous injectable solution of human immunoglobulin which is required to have a pH in the range 3.5 to 5.0. Furthermore, the ionic strength is required to be reduced to low levels, particularly below 0.001. The maintenance of the pH within this range and low ionic strength are said to be essential to the ability to store the liquid.

Formulation for extended periods, whilst satisfying criteria such as distribution of molecular size and anti-complementary activity.

Another proposal for the production of a stable liquid formulation of human immunoglobulin is contained in WO95/22990 (The Green Cross Corporation) which requires a pH in the region 5.5 in conjunction with a low electrical conductivity of less than 1 mmho.

The proposals set out in U.S. Pat. No. 4,499,073 relate to the treatment of Fraction II or Fraction III filtrate (Supernatant III) produced using the methods described originally by E. J. Cohn et al (J. Am. Chem. Soc. 68: 459–475, 1946) and, L. J. Oncley et al (J. Am. Chem. Soc. 71: 541–550, 1949). However, these conditions do not appear to be suitable for the production of a stable IgG solution derived from other cold-ethanol fractionation schemes. The pH conditions and low ionic strength specified in this reference do not result in the formation of a stable product when applied to immunoglobulin prepared according to the cold ethanol fractionation scheme used by the present applicants. Since different modified cold ethanol fractionation methods are used widely, especially in Europe, there is therefore a need for a stable IgG solution derived from starting materials other than those taught as suitable in the prior art.

It has now been surprisingly discovered that stable intravenously injectable immunoglobulin solutions may be obtained by employing quite different conditions of pH and ionic strength to those taught in the prior art, with the additional inclusion of treating the immunoglobulin preparation with an enzyme such as pepsin.

Thus, the present invention provides a liquid composition for intravenous administration which comprises a solution of an immunoglobulin in a pharmaceutically acceptable aqueous carrier, the solution having a pH in the range 5.0 to 5.8 and an ionic strength On the range 0.02 to 0.25, the immunoglobulin having been subjected to treatment with pepsin.

The ionic strength may be in the range 0.04–0.25. Ionic strength (I) is defined as half the sum of the terms obtained multiplying the concentration of ion (C) in a solution by the square of its valency (Z) ie. I=½ $\Sigma C \cdot Z-$. For example, the ionic strength of 60mM NaCl would be calculated as follows: $\frac{1}{2}[0.06 \times 1^-) + (0.06 \times 1^-)] = 0.06$ Solutions of immunoglobulin prepared according to the present invention have been measured as having conductivity values of approximately 4 mmho to over 20 mmho.

The aqueous carrier must be pharmaceutically acceptable in the sense of being compatible with other ingredients of the composition and not injurious to the patient.

The liquid composition of the present invention has the advantage of not being freeze dried. Thus, the liquid composition does not have to be reconstituted prior to use. Chemical modification of the immunoglobulin is not required nor is extensive additional purification of the Fraction II.

It has advantageously beer. found that formulation of the liquid composition according to the present invention results in a composition which is stable upon storage. Stable upon storage is taken to mean that the immunoglobulin does not substantially aggregate nor degrade and maintains acceptable levels of anti-complementary activity, PKA activity and kallikrein activity during storage for an extended period at a temperature in the range 4° C. to 25° C.

An extended period is taken to mean 12 weeks, preferably 26 weeks and most preferably 52 weeks at 25° C.; also 6 months, preferably 12 months and most preferably 24 months at 4° C.

That the composition does not substantially aggregate is taken to mean that there is an increase of no more than 2.5% to 3% in the immunoglobulin content of the preparation which has a molecular size greater than the IgG dimers present in the preparation. That the composition does not substantially degrade is taken to mean that no more than 5% to 7% of the preparation has a molecular size less than the IgG monomers present in the preparation. In addition the composition is considered to have shown acceptable levels of degradation if more than 50% of the initial antibody function (eg. anti-rubella virus activity) remains. An acceptable level of anti-complementary activity is one where the consumption of complement is not greater than 50% (1 $CH_{50}$ per milligram of immunoglobulin: for definition see protocol B attached hereto). Acceptable levels of PKA and kallikrein are not more than 35 iu per mL and less than 0.05 iu per mL respectively in a solution containing 30 g/L of immunoglobulin. Tests for distribution of molecular size, anti-complementary activity, PKA/kallikrein activity and anti rubella activity are described in the protocols A to D below.

A liquid composition which showed the stability characteristics described above would have the potential to meet certain standards (such as those referred to previously in the European Pharmacopoeia) for formulations of immunoglobulin suitable or intravenous infusion.

In accordance with the above requirements regarding acceptable levels of aggregation, anti-complementary activity, PKA/kallikrein content and antibody function, preferably the pH of the liquid composition is in the range pH 5.25–5.75 and the ionic strength is ;n the range 0.04 –0.18, more preferably 0.03–0.18.

It has now been found that pepsin treatment together with formulation of the composition as defined herein obviates any requirement to employ further purification or modification to the Fraction II material. The liquid formulation may contain residual pepsin but this can be removed if necessary.

Additionally, treatment with pepsin at low pH, eg. pH4 is particularly effective as a virus inactivation step.

The immunoglobulin of the composition is preferably IgG which may contain residual amounts of other immunoglobulins eq. IgA and/or IgM up to a level of 5% by weight of the total immunoglobulin content. However, compositions suitable for a given particular use may comprise IgA and/or IgM as required.

The immunoglobulin of the liquid composition may be obtained by way of any suitable method. For example, the immunoglobulin may be prepared according to the Cohn-Oncley cold ethanol fractionation process mentioned previously or a modified method of cold ethanol fractionation such as that described in FIG. 1. The immunoglobulin may be obtained as a Fraction II precipitate or as a supernatant (for example Supernatant III or I and III) from the fractionation process.

The Fraction II precipitate may be frozen and stored prior to resolution, removal of residual ethanol impurity, treatment with pepsin and formulation into the liquid composition suitable for intravenous administration. The ethanol impurity in the redissolved Fraction II (or supernatant I and III) may be removed, for example, by diafiltration of a solution thereof against a suitable buffer at a low pH. A suitable buffer contains for example 0.45% NaCl, 1% sucrose, and 200–400 ml 1M HCl/kg protein. Alternatively, for example, the ethanol impurity may be removed by freeze drying and the dried solids redissolved and adjusted to a low pH using a suitable titrant such as hydrochloric acid. Generally speaking the pH of the immunoglobulin solution from which the ethanol impurity has been removed is in the range 3.9 to 4.5 and preferably 3.9 to 4.1 and the residual ethanol impurity less than 10 mg/g of protein.

The solution comprising immunoglobulin may then be concentrated (eg. by ultrafiltration) to 8–12% w/w total protein and a suitable stabiliser such as a carbohydrate (eg. glucose, maltose or sucrose) added at a concentration of between one part stabiliser per one part protein (w/w) to two parts stabiliser per part protein (w/w). For example 1:1 (w/w) glucose to protein, 1.5:1 or 2:1 maltose to protein and 1.5:1 or 2:1 sucrose to protein. Other stabilisers such as amino acids (eg. glycine) may also be added at this stage at a concentration of up to 100 mg/g protein.

Incubation with a small amount of pepsin is then carried out to reduce the formation of aggregates of immunoglobulin monomer; reduce anticomplementary activity and decrease levels of PKA and kallikrein activity. Preferably pepsin is added in the range 10–150 $\mu$g/g total protein and more preferably in the range 25–100 $\mu$g/g total protein. The immunoglobulin solution is then incubated at a suitable temperature in the range 20° C. to 37° C. and preferably 35°

C. and for a suitable time in the range 1 hour to 72 hours and preferably 20–24 hours.

After incubation the pH. of the immunoglobulin solution is adjusted to between pH 5.0 to 5.8 using a suitable titrant, for example, sodium hydroxide. Preferably the pH is adjusted to between pH 5.25–5.75. The protein concentration of the solution may then be adjusted to 2–10% (w/w) and preferably to 4–6% (w/w) by dilution using a salt solution of appropriate concentration so as to bring the ionic strength of the solution to between 0.02 and 0.25. Preferably the ionic strength is adjusted to between 0.03 and 0.18. If other stabilisers such as amino acids (eg. glycine) have not been added to the composition earlier (see above) they can be included in the formulation at this stage at a concentration of up to 100 mg/g protein.

The formulated immunoglobulin solution is then filtered to remove any potential bacterial contamination and aseptically dispensed into pharmaceutically acceptable containers.

There is provided therefore a liquid composition for intravenous administration which is stable on storage and which comprises a solution in a pharmaceutically acceptable aqueous carrier of an immunoglobulin prepared from cold ethanol fractionation of plasma and which immunoglobulin does not require to be freezed dried in the final container Embodiments of the present invention will be further described by way of example, with reference to the following examples section:

EXAMPLES SECTION

Example 1

Procedure for Obtaining Immunogilobulin as Starting Material

Figure 1:
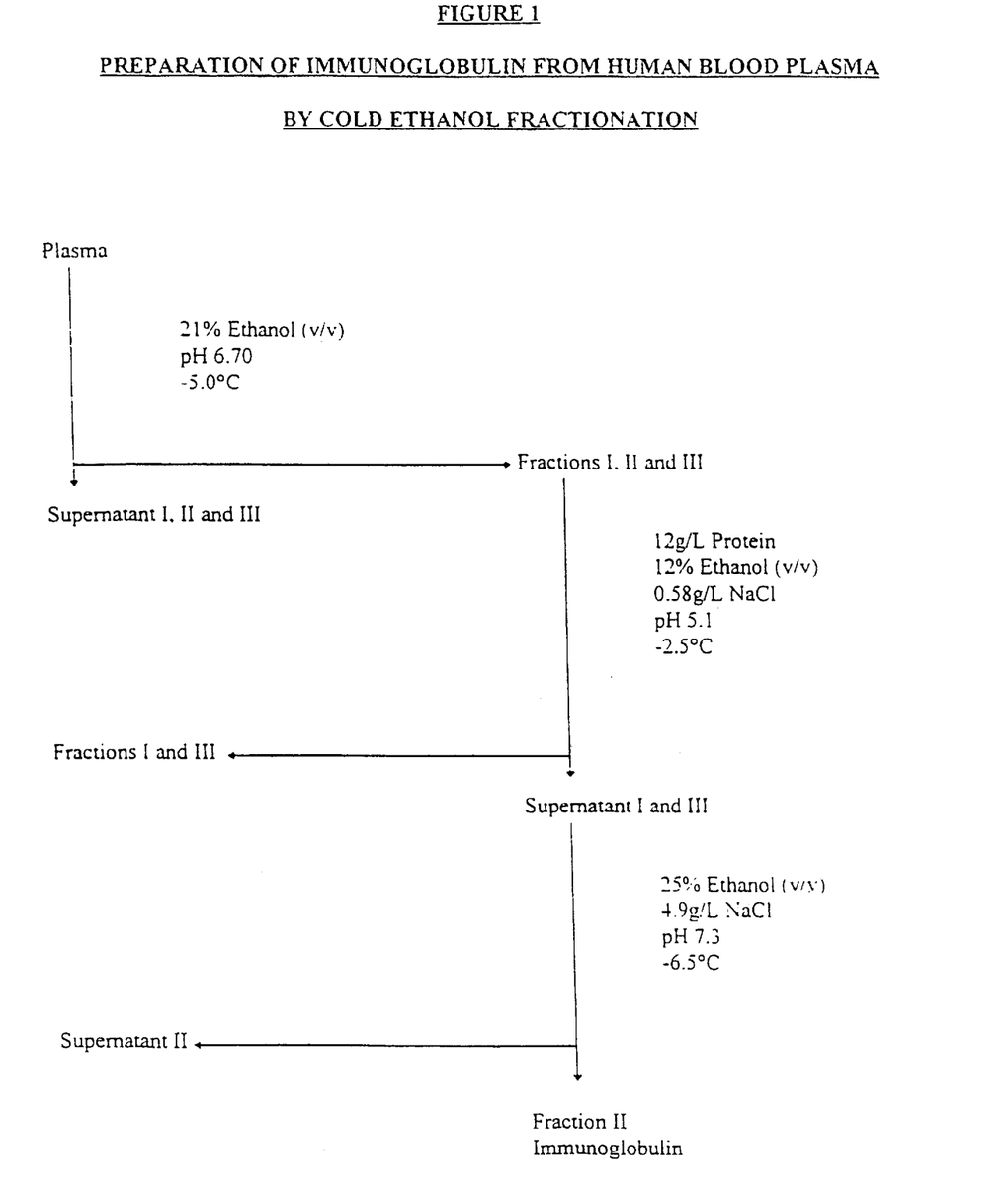

Immunoglobulin (Fraction II) is commonly prepared from human blood plasma by cold ethanol fractionation. An example of a manufacturing approach for preparing Fraction II is outlined in FIG. 1. In FIG. 1, the Fraction II is isolated using a modification of the method of Vogelaar et al (Vox Sang. 27: 193–206, 1974) from a combined Fraction I, II and III precipitate which is isolated using the Fraction II and III precipitation conditions of Hink et al (Vox Sang. 2: 174–186, 1957). The technique of preparing a combined Fraction I, II and III precipitate has been described also by Kistler and Nitschmann (Vox Sang. 7: 414–424, 1962).

Example 2

Preparation of a Liquid Immunoglobulin Composition for Intravenous Infusion

Immunoglobulin (Fraction II) prepared as above or according to any other suitable method is redissolved in sterile distilled water (3.5 L/kg paste) at 4° C. The resultant solution is then clarified by filtration (0.45 μm pore size filter) prior to ethanol removal (to ethanol <10 mg/g) and pH adjustment (pH to 4.0±0.1) by diafiltration against at least 4 volumes of 0.45% NaCl, 1% sucrose and 310–320 ml, 1M HCl/kg protein. The solution is finally concentrated to between 8 and 12% total protein by ultrafiltration The protein solution is then formulated with a stabiliser (sucrose at 2 parts per 1 part protein w/w) and a small quantity of pepsin added (0.025–0.1 mg pepsin/g protein). The pepsin-containing solution is filtered (0.45 μm pore size filter) and incubated for 21 hours at 35° C.

Following incubation, the pH of the solution is adjusted to between pH 5.0 to 5.6 using 0.25M NaOH. The protein concentration of the solution is adjusted to between 4 and 6% and the NaCl concentration to 60 mM. The final formulated liquid immunoglobulin composition is sterile filtered and aseptically dispensed into suitable containers.

Example 3

Preparation of a Liquid Immunoglobulin Composition for Intravenous infusion Formulated with an Amino Acid (glycine) as an Additional Stabiliser An immunoglobulin composition suitable for intravenous administration is prepared as in Example 2 and containing glycine at 50 mg/g as a stabiliser in addition to the formulation of the solution with sucrose prior to pepsin treatment and incubation.

Example 4

Stability of Liquid Immunoglobulin Compositions for Intravenous Infusion

A number of batches of liquid immunoglobulin of various compositions (including those described in Exanples 2 and 3) were prepared and formulated at different pH values. These compositions were tested for their stability following storage at different temperatures for varying lengths of time. The tests were carried out according to the test protocols A to D described below.

The criteria for stability were defined as follows:

Aggregation: There is an increase of no more than 2.5% in the immunoglobulin content of the preparation which has a molecular size greater than the IgG dimers present in the preparation.

Degradation: No more than 5% of the protein content of the preparation which has a molecular size less than the IgG monomers present in the preparation.

Antibody Function: There is more than 50% antibody activity (eg. anti-rubella virus) remaining compared to the initial level at the time of preparation of the composition.

Anti-complemnentary activity: The consumption of complement is no greater than 50% (1 CH: per mg of immunoglobulin for definition see protocol B attached hereto).

PKA activity: There are no more than 35 iu/mL of PKA activity in a solution of 30 g/L immunoglobulin.

Kallikrein activity: There is less than 0.05 iu/mL of kallikrein activity in a 30 g/L solution.

The results for this series of experiments are shown in Tables 1–8. The results are presented as the number of batches which are stable for the criteria indicated and at the time and temperature shown. The number of batches which had been tested for the criteria indicated at the time and temperature shown are given in parenthesis. For example, an entry of "1 (4)" against Degradation/Antibody Function for 4 weeks at 37° C. means that 1 batch out of 4 tested following storage at 37° C. for 4 weeks met the stability criteria described above for both degradation and antibody function.

Also in tables 1–8, the columns shown as shaded relate to data concerning liquid compositions prepared according to the present invention, viz compositions with a pH of 5.0–5.8, an ionic strength of 0.02 to 0.25 and which have been subjected to pepsin treatment. Data relating to immunoglobulin compositions not prepared according to the present invention and which are shown by way of comparison, are in the columns which have not been shaded.

Conclusions from the results are as follows:
Experiment I (Table 1):
5% w/v immunoglobulin (treated with pepsin at 0.1 mg/g); 10% sucrose: 60 mM NaCl; pH 4.05–6.02
When a product is formulated according to the present invention, at pH 5.25 to 5.5 in the liquid form, the product is stable for more than 26 weeks at 4° C. and passes experimental accelerated stability tests at 25° C. and 37° C.
Experiment II (Table 2):
5% w/v immunoglobulin (which has not been treated with pepsin): 10% w/v sucrose 60 mM NaCl: pH 4.25–5.25

In the absence of pepsin, a liquid formulation of pH 5.25 or less aggregates upon storage at elevated temperatures. In addition, it is known from previous work and confirmed at the pH 5.25 formulation in this experiment that pepsin is necessary to reduce PKA and Kallikrein.
Experiment III (Table 3):
5% w/v immunoglobulin (which has not been treated with pepsin); 10% w/v sucrose: 3–9 mM NaCl; pH 4,50–5.0

When immunoglobulin compositions are formulated at low pH and low ionic strength, without pepsin, the product has high PKA and Kallikrein levels which are not reduced upon storage at 25° C. and 4° C. The compositions aggregate upon storage at 37° C.

These formulation conditions are among those described by U.S. Pat. No. 4,499,073 (Cutter Laboratories Inc.) as being essential to the ability to store a liquid formulation for extended periods. The results of this experiment demonstrate that the conditions specified in U.S. Pat. No. 4,499,073 do not result in the formation of a stable product when they are applied to immunoglobulin prepared according to the cold ethanol fractionation scheme used by the present applicants.
Experiment IV (Table 4): 5% w/v immunoglobulin (treated with pepsin at 0.1 mg/g); 10% w/v sucrose 4–9 mM NaCl; pH 4.4–5.2

When immunoglobulin compositions are formulated at lower ionic strength (in the presence of pepsin) the product tends to fragment even at 4° C.
Experiment V (Table 5):
5% w/v immunoglobulin (treated with pepsin at 0.025 mg/g or 0.05 mg/g); 10% w/v sucrose; 60 mM NaCl; pH 5.25–5.75

When the pepsin concentration is reduce to 0.025 mg/g protein the product does not degrade and levels of PKA and Kallikrein are well within limits. All batches also show no aggregation on storage at elevated temperatures.
Experiment VI (Table 6):
5% w/v immunoglobulin (treated with pepsin at 0.1 mg/g). 10% w/v sucrose: 100 and 180 nM NaCl: pH 4.05–5.5

When the ionic strength of immunoglobulin compositions (which have been treated with pepsin at 0.1 mg/g protein) is increased from around 60 mmol to 180 mmol NaCl the product generally aggregates upon storage at elevated temperatures.

Experiment VII (Table 7):
5% w/v immunoglobulin (treated with pepsin at 0,025–0.1 mg/g) 10% w/v sucrose; 50 mg Glycine per a protein; 30–60 mM NaCl; pH 5.5

The preferred composition can also be formulated with an amino acid (eg. glycine) as an additional stabiliser.
Experiment VIII (Table 8):
5% w/v immunoglobulin (treated with pepsin at 0.025–0.5 mg/g 7.5–10% w/v Maltose, 50 mg Glycine per g protein, 60 mM NaCl pH 5.5

The preferred composition can also be formulated with maltose as a stabiliser; the preferred concentration of maltose is 7.5 to 10% w/v. When a product is formulated according to the present invention, at a pH in the range 5.0–5.8, ionic strength 0.02–0.25 and subjected to pepsin treatment, in the presence of either maltose or sucrose the product is stable for more than 26 weeks at 4° C. and passes experimental accelerated stability tests at 25° C. and 37° C.

On the basis of the data obtained from the various compositions tested, a composition as defined previously herein (ie. formulated at a pH in the range 5.0–5.8, ionic strength 0.02–0.25 and subjected to pepsin treatment) is determined to be stable in terms of acceptable aggregation, degradation, anti-complementary activity, PKA content and kallikrein content.

TEST PROTOCOLS

A. Distribution of Molecular Size

The molecular size distribution of the immunoglobulin product is measured by size exclusion using high performance liquid chromatography. The product is analysed on a Pye Unicam modular system using a TSK G3000 SW-XL gel filtration column of dimensions 7.8×300 mm with a guard column (7.8×40 mM) composed of the same material. Samples are diluted to 5–10 g/L in the mobile phase (0.2M potassium phosphate buffer pH 7.0) and filtered through 0.45 $\mu$m membrane before 20 $\mu$L is injected. Protein is eluted at 0.4 mL/min and detected by UV absorption at 280 nm. The traces obtained are analysed by manual triangulation according to criteria described in the European Pharmacopoeia.

Peak areas corresponding to aggregate (retention time 15–18 minutes), dimer (18.5–19.5 min), monomer (21.0–22.0 min) and fragments (any material eluting after the monomer peak and before the salt front) are identified and quantified as a percentage of the total elution area.

B. Anti-Complementary activity

The level of spontaneous (antigen independent) activation of complement by immunoglobulin preparations is measured by the degree of inhibition of lysins of sensitised sheep red blood cells by a fixed amount of complement according to the method of Frommhagen and Findenberg (J. Immunol 89: 336–343, 1962).

In summary, a se. amount of guinea-pig complement is incubated with a series of dilutions of the samples under test. After a period of incubation (60 minutes at 37° C.) the amount of complement inactivated by the test samples is determined by adding an equal amount of sensitised sheep erythrocytes to each tube and measuring the degree of haemolysis. The dilution of the test sample in which 50% haemolysis occurs is also that dilution which has consumed 50% of the complement present. From the protein concentration of this sample the anti complementary activity can be calculated as the mg of protein required to consume 1CH, unit (complement required for 50% of lysis of 10° sheep red blood cells).

C. Prekallikrein Activator Activity and Kallikrein Activity

The level of PKA activity in the immunoglobulin product is measured according to the method of Alving and co-workers (J. Lab Clin Med. 96: 334–346, 1980).

In summary the measurement of PKA activity is carried out by a two stage procedure; the first stage involves the conversion of prekallikrein to kallikrein by the material being analysed. In the second stage the generated kallikrein is measured by its rate of hydrolysis of the synthetic substrate S2303 (Kabi Diagnostics, Sweden) by an end point incubation assay. The PKA activity is compared to that of the UK Reference 1 preparation (a plasma protein fraction which contains 75 International Units PKA).

The kallikrein activity generated by PKA in the sample is measured by subtracting the activity determined in the absence of prekallikrein from that measured in its presence. The kallikrein concentration is recorded in units/ml where one unit is that amount of kallikrein which will hydrolyse 0.2 mM S2302 at an initial rate of 1 μmol/minute at pH 8.0 and 37° C.

In practice 10 μl of test solution is incubated with 90 μl prekallikrein reagent (prepared by the method of Lundblad (Develop. Biol. Stand. 44: 107–114, 1979] at pH 8.0 and 37° C. for 60 minutes. 500 μl S2302 is then added and incubation continued for a further 10 minutes when the reaction is stopped by the addition of 100 μl 10% acetic acid. All samples, standards and controls are assayed in duplicate and each sample and control includes a kallikrein blank (assay buffer added instead of prekallikrein reagent). The absorbance of each solution is then read at 405 mM, and a standard curve from the mean optical densities of the standards is constructed. The mean absorbance of the blanks is subtracted from the mean absorbance of the test solutions and the PKA concentrations calculated from the standard curve.

D. Antibody Function (Anti-Rubella virus Activity)

Anti-rubella antibody is quantified by a haemolysis in gel technique. This is a complement mediated assay which measures the functional integrity of anti-rubella antibodies present, relying on both antigen binding and antigen mediated complement binding properties of the immunoglobulin preparation.

In summary, red blood cells are sensitised by coating their surfaces with rubella antigen, these are then suspended in agarose and poured into plates. When the mixture has solidified wells are cut and filled with the samples and standards to be tested. During overnight incubation at 4° C. the samples diffuse into the agarose and any specific antibody present complexes with the antigen on the surfaces of the red blood cells. The gel is then flooded with guinea-pig complement and incubated at 37° C. Antigen-antibody complexes activate the complement which results in lysis of the red blood cells. This is manifest by a clear circular area surrounding the well; the area of the zone of haemolysis being proportional to $\log_{10}$ of the antibody concentration. Dilutions of the sample to be tested are assayed in parallel with dilutions of a standard (previously calibrated against the WHO International Standard) and from a plot of the diffusion zone areas of the standards against the antibody concentration, the anti-rubella antibody concentrations of the samples under test are calculated.

TABLE 1

STABILITY OF LIQUID IMMUNOGLOBULIN COMPRISING 5% w/w IMMUNOGLOBULIN (TREATED WITH PEPSIN AT 0.1 mg/g), 10% SUCROSE, 60 mM NaCl AT A pH IN THE RANGE 4.05–6.02

| TEST OF STABILITY | NUMBER OF BATCHES PASSING (Numer of Batches Tested) | | | | | | |
|---|---|---|---|---|---|---|---|
| | pH 4.05 | pH 4.5 | pH 5.0 | pH 5.25 | pH 5.5 | pH 5.8 | pH 6.02 |
| Aggregation/Anti Complementary Activity | | | | | | | |
| 4 weeks, 37° C. | 2 (2) | 1 (1) | 3 (4) | 8 (8) | 7 (7) | 1 (2) | 1 (2) |
| 12 weeks, 25° C. | 2 (2) | 1 (1) | 3 (4) | 8 (8) | 8 (8) | 2 (2) | 2 (2) |
| 26 weeks, 4° C. | 2 (2) | 1 (1) | 3 (3) | 8 (8) | 7 (7) | 1 (2) | 2 (2) |
| 52 weeks, 4° C. | ND* | ND | 1 (1) | 6 (6) | 4 (4) | 1 (1) | 1 (1) |
| Fragmentation/Anti-Rubella | | | | | | | |
| 4 weeks, 37° C. | 2 (2) | 1 (1) | 4 (4) | 8 (8) | 7 (7) | 1 (2) | 1 (2) |
| 12 weeks, 25° C. | 2 (2) | 1 (1) | 4 (4) | 8 (8) | 7 (8) | 1 (2) | 1 (2) |
| 26 weeks, 4° C. | 2 (2) | 1 (1) | 3 (3) | 7 (8) | 7 (7) | 2 (2) | 2 (2) |
| 52 weeks, 4° C. | ND | ND | 1 (1) | 6 (6) | 4 (4) | 1 (1) | 1 (1) |
| PKA/Kallikrein | | | | | | | |
| 4 weeks, 37° C. | 1 (1) | 1 (1) | 2 (2) | 2 (2) | 2 (2) | ND | ND |
| 12 weeks, 25° C. | 2 (2) | 1 (1) | 3 (3) | 6 (6) | 5 (5) | 1 (1) | 1 (1) |
| 26 weeks, 4° C. | 2 (2) | 1 (1) | 2 (2) | 7 (7) | 2 (2) | 1 (1) | 1 (1) |
| 52 weeks, 4° C. | ND | ND | ND | 6 (6) | 1 (2) | 1 (1) | 1 (1) |

*ND: Not determined

TABLE 2

STABILITY OF LIQUID IMMUNOGLOBULIN COMPOSITIONS COMPRISING 5% w/w IMMUNOGLOBULIN (NOT PEPSIN TREATED) 10% SUCROSE, 60mM NaCl AT A pH IN THE RANGE 4.25–5.52

| TEST OF STABILITY | NUMBER OF BATCHES PASSING (Numer of Batches Tested) | | | |
|---|---|---|---|---|
| | pH 4.05 | pH 4.5 | pH 5.0 | pH 5.25 |
| Aggregation/Anti Complementary Activity | | | | |
| 4 weeks, 37° C. | 0 (1) | 0 (1) | 0 (1) | 0 (1) |
| 12 weeks, 25° C. | 0 (1) | 0 (1) | 0 (1) | 1 (1) |
| 26 weeks, 4° C. | 1 (1) | 1 (1) | 1 (1) | 1 (1) |
| 52 weeks, 4° C. | 1 (1) | 1 (1) | 1 (1) | 0 (1) |
| Fragmentation/Anti-Rubella | | | | |
| 4 weeks, 37° C. | 1 (1) | 1 (1) | 1 (1) | 1 (1) |
| 12 weeks, 25° C. | 1 (1) | 1 (1) | 1 (1) | 1 (1) |
| 26 weeks, 4° C. | 1 (1) | 1 (1) | 1 (1) | 1 (1) |
| 52 weeks, 4° C. | 1 (1) | 1 (1) | 1 (1) | 1 (1) |
| PKA/Kallikrein | | | | |
| 4 weeks, 37° C. | 1 (1) | 1 (1) | 1 (1) | 0 (1) |
| 12 weeks, 25° C. | 1 (1) | 1 (1) | ND | 0 (1) |
| 26 weeks, 4° C. | 1 (1) | 0 (1) | 1 (1) | 0 (1) |
| 52 weeks, 4° C. | 1 (1) | 1 (1) | 1 (1) | ND |

*ND: Not determined

TABLE 3

STABILITY OF LIQUID IMMUNOGLOBULIN COMPOSITIONS COMPRISING 5% w/w IMMUNOGLOBULIN (NOT PEPSIN TREATED) 10% SUCROSE, 3–9 mM NaCl AT A pH IN THE RANGE 4.50–5.25

| TEST OF STABILITY | NUMBER OF BATCHES PASSING (Numer of Batches Tested) | | |
|---|---|---|---|
| | pH 4.50 | pH 4.7 | pH 5.25 |
| Aggregation/Anti Complementary Activity | | | |
| 4 weeks, 37° C. | 0 (3) | 0 (1) | 0 (1) |
| 12 weeks, 25° C. | 0 (3) | 1 (1) | 1 (1) |
| 26 weeks, 4° C. | 3 (3) | 1 (1) | 1 (1) |
| 52 weeks, 4° C. | 3 (3) | 1 (1) | 1 (1) |
| Fragmentation/Anti-Rubella | | | |
| 4 weeks, 37° C. | 3 (3) | 1 (1) | 1 (1) |
| 12 weeks, 25° C. | 3 (3) | 1 (1) | 1 (1) |
| 26 weeks, 4° C. | 3 (3) | 1 (1) | 1 (1) |
| 52 weeks, 4° C. | 3 (3) | 1 (1) | 1 (1) |
| PKA/Kallikrein | | | |
| 4 weeks, 37° C. | 3 (3) | 1 (1) | 0 (1) |
| 12 weeks, 25° C. | 0 (3) | 0 (1) | 0 (1) |
| 26 weeks, 4° C. | 0 (3) | 0 (1) | 0 (1) |
| 52 weeks, 4° C. | 0 (3) | 0 (1) | 0 (1) |

TABLE 4

STABILITY OF LIQUID IMMUNOGLOBULIN COMPOSITIONS COMPRISING 5% w/w IMMUNOGLOBULIN (TREATED WITH PEPSIN AT 0.1 mg/g), 10% SUCROSE, 4–9 mM NaCl AT A pH IN THE RANGE 4.4–5.2

| TEST OF STABILITY | NUMBER OF BATCHES PASSING (Numer of Batches Tested) | | |
|---|---|---|---|
| | pH 4.4 | pH 4.7 | pH 5.2 |
| Aggregation/Anti Complementary Activity | | | |
| 4 weeks, 37° C. | 1 (1) | 1 (1) | 1 (1) |
| 12 weeks, 25° C. | 1 (1) | 1 (1) | 1 (1) |
| 26 weeks, 4° C. | 1 (1) | 1 (1) | 1 (1) |
| 52 weeks, 4° C. | 1 (1) | 1 (1) | 1 (1) |
| Fragmentation/Anti-Rubella | | | |
| 4 weeks, 37° C. | 0 (1) | 0 (1) | 0 (1) |
| 12 weeks, 25° C. | 0 (1) | 0 (1) | 0 (1) |
| 26 weeks, 4° C. | 0 (1) | 0 (1) | 0 (1) |
| 52 weeks, 4° C. | 0 (1) | 0 (1) | 0 (1) |
| PKA/Kallikrein | | | |
| 4 weeks, 37° C. | ND* | ND | ND |
| 12 weeks, 25° C. | ND | ND | ND |
| 26 weeks, 4° C. | ND | ND | ND |
| 52 weeks, 4° C. | ND | ND | ND |

*ND: Not determined

TABLE 5

STABILITY OF LIQUID IMMUNOGLOBULIN COMPOSITIONS COMPRISING 5% w/w IMMUNOGLOBULIN (TREATED WITH PEPSIN AT 0.025 mg/g or 0.05 mg/g), 10% SUCROSE, 60 mM NaCl AT A pH IN THE RANGE 5.25–5.75

| TEST OF STABILITY | NUMBER OF BATCHES PASSING (Numer of Batches Tested) | | | | |
|---|---|---|---|---|---|
| | pH 5.25 0.025 mg pepsin/g | pH 5.25 0.05 mg pepsin/g | pH 5.50 0.025 mg pepsin/g | pH 5.50 0.05 mg pepsin/g | pH 5.75 0.25 mg pepsin/g |
| Aggregation/Anti Complementary Activity | | | | | |
| 4 weeks, 37° C. | 3 (3) | 2 (2) | 3 (3) | 2 (2) | 1 (1) |
| 12 weeks, 25° C. | 3 (3) | 2 (2) | 3 (3) | 2 (2) | 1 (1) |
| 26 weeks, 4° C. | 2 (2) | 2 (2) | 3 (3) | 2 (2) | 1 (1) |
| 52 weeks, 4° C. | 1 (1) | 2 (2) | 2 (2) | 2 (2) | ND |
| Fragmentation/ Anti-Rubella | | | | | |
| 4 weeks, 37° C. | 3 (3) | 2 (2) | 2 (2) | 1 (1) | 1 (1) |
| 12 weeks, 25° C. | 3 (3) | 2 (2) | 3 (3) | 2 (2) | 1 (1) |
| 26 weeks, 4° C. | 2 (2) | 2 (2) | 3 (3) | 2 (2) | 1 (1) |
| 52 weeks, 4° C. | 1 (1) | 2 (2) | 2 (2) | 2 (2) | ND |
| PKA/Kallikrein | | | | | |
| 4 weeks, 37° C. | 3 (3) | 2 (2) | 1 (1) | ND* | 1 (1) |
| 12 weeks, 25° C. | 3 (3) | 2 (2) | 1 (1) | ND | 1 (1) |
| 26 weeks, 4° C. | 3 (3) | 2 (2) | 1 (1) | ND | 1 (1) |
| 52 weeks, 4° C. | 1 (1) | 1 (1) | ND | ND | ND |

*ND: Not determined

TABLE 6

STABILITY OF LIQUID IMMUNOGLOBULIN COMPOSITIONS COMPRISING 5% w/w IMMUNOGLOBULIN (TREATED WITH PEPSIN AT 0.1 mg/g), 10% SUCROSE, 100 AND 180 mM NaCl AT A pH IN THE RANGE 4.05–5.5

| TEST OF STABILITY | NUMBER OF BATCHES PASSING (Number of Batches Tested) | | | | |
|---|---|---|---|---|---|
| | pH 4.05–4.30 180 mM NaCl | pH 5.0 180 mM NaCl | pH 5.5 180 mM NaCl | pH 4.20 100 mM NaCl | pH 5.1–5.6 100 mM NaCl |
| Aggregation/Anti Complementary Activity | | | | | |
| 4 weeks, 37° C. | 1 (2) | 1 (2) | 1 (2) | 0 (1) | 3 (4) |
| 12 weeks, 25° C. | 0 (2) | 0 (2) | 1 (2) | 0 (1) | 4 (4) |

TABLE 6-continued

STABILITY OF LIQUID IMMUNOGLOBULIN
COMPOSITIONS COMPRISING 5% w/w IMMUNOGLOBULIN
(TREATED WITH PEPSIN AT 0.1 mg/g), 10% SUCROSE,
100 AND 180 mM NaCl AT A pH IN THE RANGE 4.05–5.5

|  | NUMBER OF BATCHES PASSING (Number of Batches Tested) | | | | |
| --- | --- | --- | --- | --- | --- |
| TEST OF STABILITY | pH 4.05–4.30 180 mM NaCl | pH 5.0 180 mM NaCl | pH 5.5 180 mM NaCl | pH 4.20 100 mM NaCl | pH 5.1–5.6 100 mM NaCl |
| 26 weeks, 4° C. | 1 (2) | 0 (2) | 1 (2) | 0 (1) | 2 (3) |
| 52 weeks, 4° C. | 0 (2) | 2 (2) | 2 (2) | 0 (1) | 2 (2) |
| Fragmentation/Anti-Rubella | | | | | |
| 4 weeks, 37° C. | 1 (2) | 2 (2) | 2 (2) | 0 (1) | 1 (4) |
| 12 weeks, 25° C. | 0 (2) | 2 (2) | 2 (2) | 0 (1) | 3 (4) |
| 26 weeks, 4° C. | 1 (2) | 2 (2) | 2 (2) | 1 (1) | 3 (3) |
| 52 weeks, 4° C. | 2 (2) | 2 (2) | 2 (2) | 1 (1) | 2 (2) |
| PKA/Kallikrein | | | | | |
| 4 weeks, 37° C. | ND | 1 (1) | 1 (1) | ND | ND |
| 12 weeks, 25° C. | ND | 1 (1) | 1 (1) | 1 (1) | 2 (2) |
| 26 weeks, 4° C. | 1 (1) | 1 (1) | 1 (1) | ND | ND |
| 52 weeks, 4° C. | 1 (1) | 1 (1) | 1 (1) | ND | ND |

*ND: Not determined

TABLE 7

STABILITY OF LIQUID IMMUNOGLOBULIN
COMPOSITIONS COMPORISING 5% w/w IMMUNOGLOBULIN
(TREATED WITH PEPSIN AT 0.025 mg/g–0.1 mg/g),
10% SUCROSE, 50 mg/g GLYCINE, 40–60 mM NaCl AT pH 5.50

|  | NUMBER OF BATCHES PASSING (Numer of Batches Tested) | |
| --- | --- | --- |
| TEST OF STABILITY | 0.1 mg pepsin/g 30.40 mM NaCl | 0.1 mg pepsin/g 60 mM NaCl |
| Aggregation/Anti Complementary Activity | | |
| 4 weeks, 37° C. | 4 (4) | 2 (2) |
| 12 weeks, 25° C. | 2 (2) | 2 (2) |
| 12 weeks, 4° C. | 2 (2) | 2 (2) |
| Fragmentation/Anti-Rubella | | |
| 4 weeks, 37° C. | 4 (4) | 2 (2) |
| 12 weeks, 25° C. | 2 (2) | 2 (2) |
| 12 weeks, 4° C. | 2 (2) | 2 (2) |
| PKA/Kallikrein | | |
| 4 weeks, 37° C. | 1 (1) | ND |
| 12 weeks, 25° C. | ND* | ND |
| 12 weeks, 4° C. | ND | ND |

*ND: Not determined

TABLE 8

STABILITY OF LIQUID IMMUNOGLOBULIN
COMPOSITIONS COMPORISING 5% w/w IMMUNOGLOBULIN
(TREATED WITH PEPSIN AT 0.025 mg/g OR 0.1 mg/g), 10% MALTOSE
(WITH OR WITHOUT 50 mg GLYCINE/g PROTEIN)
OR 7.5% MALTOSE (WITH 50 mg GLYCINE/g), 60 mM NaCl AT pH 5.5

|  | NUMBER OF BATCHES PASSING (Number of Batches Tested) | | | | |
| --- | --- | --- | --- | --- | --- |
|  | 0.1 mg pepsin/g protein | | 0.025 mg pepsin/g protein | | |
|  | 10% Maltose | 7.5% Maltose | 10% Maltose | 7.5% Maltose | |
| TEST OF STABILITY | 50 mg Glycine/g | No Glycine | 50 mg Glycine/g | 50 mg Glycine/g | 50 mg Glycine/g |
| Aggregation/Anti Complementary Activity | | | | | |
| 4 weeks, 37° C. | 1 (1) | 2 (2) | 1 (1) | 1 (1) | 1 (1) |
| 12 weeks, 25° C. | ND | 2 (2) | 1 (1) | 1 (1) | 1 (1) |
| 26 weeks, 4° C. | ND | 2 (2) | 1 (1) | 1 (1) | 1 (1) |

TABLE 8-continued

STABILITY OF LIQUID IMMUNOGLOBULIN
COMPOSITIONS COMPORISING 5% w/w IMMUNOGLOBULIN
(TREATED WITH PEPSIN AT 0.025 mg/g OR 0.1 mg/g), 10% MALTOSE
(WITH OR WITHOUT 50 mg GLYCINE/g PROTEIN)
OR 7.5% MALTOSE (WITH 50 mg GLYCINE/g), 60 mM NaCl AT pH 5.5

| | NUMBER OF BATCHES PASSING (Number of Batches Tested) | | | | |
|---|---|---|---|---|---|
| | 0.1 mg pepsin/g protein | | | 0.025 mg pepsin/g protein | |
| | 10% Maltose | | 7.5% Maltose | 10% Maltose | 7.5% Maltose |
| TEST OF STABILITY | 50 mg Glycine/g | No Glycine | 50 mg Glycine/g | 50 mg Glycine/g | 50 mg Glycine/g |
| Fragmentation/Anti-Rubella | | | | | |
| Complementary Activity | 1 (1) | 2 (2) | 1 (1) | 1 (1) | 1 (1) |
| 4 weeks, 37° C. | ND | 2 (2) | 1 (1) | 1 (1) | 1 (1) |
| 12 weeks, 25° C. | ND | 2 (2) | 1 (1) | 1 (1) | 1 (1) |
| 26 weeks, 4° C. | | | | | |
| PKA/Kallikrein | | | | | |
| 4 weeks, 37° C. | ND | ND | ND | ND | ND |
| 12 weeks, 25° C. | ND | ND | ND | ND | ND |
| 26 weeks, 4° C. | ND | ND | 1 (1) | ND | ND |

What is claimed is:

1. A liquid composition for intravenous administration comprising a solution of an immunoglobulin, which comprises IgG monomers and IgG dimers, in a pharmaceutically acceptable aqueous carrier, the solution having a pH in the range of 5.0 to 5.8 and an ionic strength in the range 0.02 to 0.25, wherein the immunoglobulin has been subjected to treatment with pepsin, wherein the liquid composition is devoid of non-tenside amphiphilic stabilizers, and wherein the liquid composition is stable upon storage for 6 months at 4° C.

2. A liquid composition according to claim 1 wherein, after storage for 6 months at 4° C., there is an increase of no more than 2.5% in the immunoglobulin content of the composition having a molecular size greater than the IgG dimers present in the composition.

3. A liquid composition according to claim 1 wherein, after storage for 6 months at 4° C., no more than 5% of the composition has a molecular size less than the IgG monomers present in the composition.

4. A liquid composition according to claim 1 wherein more than 50% of the initial antibody function of the composition remains after storage for 6 months at 4° C.

5. A liquid composition according to claim 1 wherein, after storage for 6 months at 4° C., the pre-kallikrein activator (PKA) level of the composition is not more than 35 iu per mL in a composition containing 30 g/L of immunoglobulin.

6. A liquid composition according to claim 1 wherein, after storage for 6 months at 4° C., the kallikrein level is less than 0.5 iu per mL in a composition containing 30 g/L of immunoglobulin.

7. A liquid composition according to claim 1 wherein the composition is stable upon storage for 12 months at 4° C.

8. A liquid composition according to claim 1 wherein the composition is stable upon storage for 24 months at 4° C.

9. A liquid composition according to claim 1 wherein the pH is in the range of 5.25 to 5.75.

10. A liquid composition according to claim 1 wherein the ionic strength is in the range 0.03 to 0.18.

11. A liquid composition according to claim 1 wherein the ionic strength is in the range 0.04 to 0.18.

12. A liquid composition according to claim 1 wherein the treatment with pepsin is carried out at a pH of from 3.9 to 4.5.

13. A liquid composition according to claim 1 wherein pepsin has been added in the range 10–15 μg/g total protein.

14. A liquid composition according to claim 1 wherein the treatment with pepsin is carried out at a temperature in the range 20° C. to 37° C. and for a time in the range 1 hour to 72 hours.

15. A liquid composition according to claim 1, wherein the immunoglobulin further comprises IgA and/or IgM.

16. A liquid composition according to claim 15, wherein up to 5% by weight of the total immunoglobulin content of the composition is IgA and/or IgM.

17. A liquid composition according to claim 1 wherein the solution immunoglobulin is prepared from a cold ethanol fractionation process of plasma.

18. A liquid composition according to claim 1 wherein the solution of. immunoglobulin comprises 8–12% w/w total protein.

19. A liquid composition according to claim 1 wherein the solution of the immunoglobulin comprises a suitable stabilizer added at a concentration of one part stabilizer per one part protein (w/w) to two parts stabilizer per one part protein (w/w).

20. A liquid composition according to claim 19 wherein the stabilizer is a carbohydrate.

21. A liquid composition according to claim 20 wherein the carbohydrate is glucose.

22. A liquid composition according to claim 21 wherein the carbohydrate is present in a concentration of 1:1 (w/w) carbohydrate to protein.

23. A liquid composition according to claim 20 wherein the carbohydrate is maltose or sucrose.

24. A liquid composition according to claim 23 wherein the carbohydrate is present in a concentration of 1.5:1 (w/w) carbohydrate to protein.

25. A liquid composition according to claim 23 wherein the carbohydrate is present in a concentration of 2:1 (w/w) carbohydrate to protein.

26. A liquid composition according to claim 19 wherein the solution of immunoglobulin further comprises glycine at a concentration of up to 100 mg/g protein.

27. A liquid composition for intravenous administration comprising a solution of an immunoglobulin in a pharmaceutically acceptable aqueous carrier, the solution having a pH in the range of 5.25 to 5.75 and an ionic strength in the range 0.03 to 0.18, wherein the immunoglobulin has been subjected to treatment with pepsin, wherein the liquid composition is devoid of non-tenside amphiphilic stabilizers, and wherein the liquid composition is stable upon storage for 6 months at 4° C.

28. A liquid composition for intravenous administration comprising a solution of an immunoglobulin in a pharmaceutically acceptable aqueous carrier, the solution having a pH in the range of 5.25 to 5.75 and an ionic strength in the range 0.03 to 0.18, wherein the immunoglobulin has been subjected to treatment with pepsin, wherein the liquid composition is devoid of non-tenside amphiphilic stabilizers, and wherein the liquid composition is stable upon storage for 12 months at 4° C.

29. A liquid composition for intravenous administration comprising a solution of an immunoglobulin in a pharmaceutically acceptable aqueous carrier, the solution having a pH in the range of 5.25 to 5.75 and an ionic strength in the range 0.03 to 0.18, wherein the immunoglobulin has been subjected to treatment with pepsin, wherein the liquid composition is devoid of non-tenside amphiphilic stabilizers, and wherein the liquid composition is stable upon storage for 24 months at 4° C.

* * * * *